(12) United States Patent
Bauer

(10) Patent No.: US 8,802,145 B2
(45) Date of Patent: Aug. 12, 2014

(54) HIGHLY POROUS, FAST-DISINTEGRATING SOLID DOSAGE FORM AND ITS WAY OF MANUFACTURING COMPRISING THE PREPARATION OF A POWDER AND A FREEZEDRYING STEP

(75) Inventor: Kurt Heinz Bauer, Freiburg (DE)

(73) Assignee: Pantec AG, Stans (CH)

( * ) Notice: Subject to any disclaimer, the term of this patent is extended or adjusted under 35 U.S.C. 154(b) by 881 days.

(21) Appl. No.: 11/666,434

(22) PCT Filed: Oct. 27, 2005

(86) PCT No.: PCT/EP2005/055591
§ 371 (c)(1),
(2), (4) Date: Apr. 27, 2007

(87) PCT Pub. No.: WO2006/045830
PCT Pub. Date: May 4, 2006

(65) Prior Publication Data
US 2009/0062241 A1    Mar. 5, 2009

(30) Foreign Application Priority Data
Oct. 28, 2004  (EP) .................................. 04105381

(51) Int. Cl.
| | | |
|---|---|---|
| *A61K 9/00* | (2006.01) | |
| *A61K 31/60* | (2006.01) | |
| *A61K 31/451* | (2006.01) | |
| *A61K 31/606* | (2006.01) | |
| *A61K 31/192* | (2006.01) | |
| *A61K 31/341* | (2006.01) | |
| *A61K 9/46* | (2006.01) | |

(52) U.S. Cl.
CPC ............. *A61K 9/0056* (2013.01); *A61K 9/0007* (2013.01)

USPC ........... 424/486; 514/166; 514/570; 514/165; 424/441

(58) Field of Classification Search
None
See application file for complete search history.

(56) References Cited

U.S. PATENT DOCUMENTS 4,371,516 A * 2/1983 Gregory et al. ............... 424/485
5,178,878 A * 1/1993 Wehling et al. ............... 424/466
(Continued)

FOREIGN PATENT DOCUMENTS

JP           9-48726          2/1997

OTHER PUBLICATIONS

Menyhart, L., Lyophilization: Freeze-Drying: Donstream Process. 1995, [online] retrieved from http://128.113.2.9/dept/chem-eng/Biotech-Environ/DOWNSTREAM/index.htm on Jan. 12, 2011; 5 pages.*

(Continued)

*Primary Examiner* — Richard Schnizer
*Assistant Examiner* — Katherine Peebles
(74) *Attorney, Agent, or Firm* — Wenderoth, Lind & Ponack, L.L.P.

(57) ABSTRACT

The invention relates to a method of manufacture of fast-disintegrating solid dosage forms, characterized in that one or more structure building components in mixed solid powder form are dosed into cavities of blister packs or moulds, the remaining components dissolved in water dosed and added to the powder to form a moistened, plasticized mass, frozen to below −20° C., and the water sublimed in high vacuum. In this way solid dosage forms are obtained with a similar porous structure as usually result from freeze drying processes, but the process requires much less water, which means considerably less time and less energy.

13 Claims, 2 Drawing Sheets

(56) References Cited

U.S. PATENT DOCUMENTS

| | | |
|---|---|---|
| 5,976,577 A | 11/1999 | Green et al. |
| 6,509,040 B1 | 1/2003 | Murray et al. |
| 6,602,520 B1* | 8/2003 | Schroeder et al. ............ 424/466 |
| 2001/0055611 A1 | 12/2001 | Green et al. |
| 2002/0098198 A1* | 7/2002 | Watts et al. ................ 424/185.1 |
| 2002/0131998 A1* | 9/2002 | Martani ........................ 424/464 |
| 2003/0087017 A1* | 5/2003 | Hanselmann et al. ........ 426/564 |
| 2005/0036977 A1 | 2/2005 | Gole et al. |

OTHER PUBLICATIONS

Dictionary.com. Reconstitution Definition [online]. Dictionary.com, 2007 [retrieved on Mar. 18, 2014]. Retrieved from the Internet: <URL: http://dictionary.reference.com/browse/reconstitution>.*

\* cited by examiner

HIGHLY POROUS, FAST-DISINTEGRATING SOLID DOSAGE FORM AND ITS WAY OF MANUFACTURING COMPRISING THE PREPARATION OF A POWDER AND A FREEZEDRYING STEP

FIELD OF THE INVENTION

The invention relates to an economical method of manufacture of highly porous, fast-disintegrating solid dosage forms by partial lyophilisation, and dosage forms obtained.

BACKGROUND ART

The art of tablet making involves the making of a composition containing an active ingredient which is sturdy for packaging and handling, and disintegrable in a predictable manner.

Fast-dissolving and fast-disintegrating tablets are especially important in the field of orally ingested drugs. Many people are unwilling and/or unable to swallow tablets, capsules or other traditional solid dosage forms. This is especially the case of pharmaceuticals for paediatric or geriatric use.

One approach suitable for these persons is the use of effervescent tablets or granules. However, the use of effervescent tablets requires preparatory steps before administration of the drug and the presence of water and a suitable mixing container. In addition, the manufacture and stability of effervescent tablets is often problematic. Another possibility is the use of a chewing gum or chewing tablet containing a drug capable of absorption through the buccal cavity (U.S. Pat. No. 5,225,197). Substantial disadvantages inherent in such a delivery system are that many active drug ingredients are not suitable for buccal absorption and that many persons are not able to chew gums or tablets because of braces, dental work, and the like. Furthermore, gums are often difficult to prepare.

Two main technologies are presently used to obtain pharmaceutical dosage forms for fast disintegration on contact with saliva in the buccal cavity. These methods are summarized in M. Sugimoto, K. Matsubara, Y. Koida und M. Kobayashi, Pharm. Dev. Technol. 6 (4), 487-493 (2001):

(1) The active ingredient is mixed with water-soluble diluents and compressed on a tableting machine at low to medium compression force. This is the more conventional approach, and very often does not give tablets with the required tensile strength and reasonable disintegration time. A more recent approach is the OraSolv™ technology, which involves incorporating microencapsulated drug ingredients into a tablet obtained by compression (U.S. Pat. No. 5,178,878). The tablets have to be packed into special peel-off blister packs because their mechanical resistance is insufficient in normal blister packs. Rapidly dissolving tablets have been produced using suitable crystalline sugar structures under adapted curing conditions (U.S. Pat. No. 5,866,163). Further compressed, rapidly dissolvable dosage forms including an active ingredient and a matrix composed of a nondirect compression filler and a lubricant are disclosed in U.S. Pat. No. 6,221,392.

(2) A suspension is prepared with the active ingredient and appropriate excipients. The suspension is dispensed into blister packs and freeze-dried (U.S. Pat. No. 4,371,516). This approach usually gives tablets with porous structure, reasonable tensile strength and disintegration time, but is time-consuming and requires a costly freeze drying process. A corresponding process marketed under the term Zydis® Technology is protected by U.S. Pat. No. 4,642,903 and EP 295 242. Particular forms of this technology are protected e.g. in U.S. Pat. Nos. 5,976,577; 6,156,359; 6,413,549; 6,423,342; 6,509,040; and 6,709.669.

The effectiveness of a freeze-drying process always depends on the physico-chemical parameters of the active substances used. Replacing the freeze-drying step by conventional drying at room temperature or elevated temperature, also drying with microwave radiation, is disclosed in International Patent Application WO 97/38679, but is likewise time and energy-consuming, and is also limited to active substances which survive such conditions. A convenient procedure to overcome these drawbacks is described in European Patent Application EP03405901.4.

SUMMARY OF THE INVENTION

The invention relates to a method of manufacture of fast-disintegrating solid dosage forms, characterized in that one or more structure building components in mixed solid powder form are dosed into cavities of blister packs or moulds, the remaining components dissolved in water dosed and added to the powder to form a moistened, plasticized mass, frozen to below −20° C., and the water sublimed in high vacuum. In this way solid dosage forms are obtained with a similar porous structure as usually result from freeze-drying processes, but the process requires much less water, which means considerably less time and less energy. The invention further relates to the dosage forms obtained in such a method. In particular the invention relates to fast-disintegrating drug dosage forms for oral use.

DETAILED DESCRIPTION OF THE INVENTION

Figure 1:
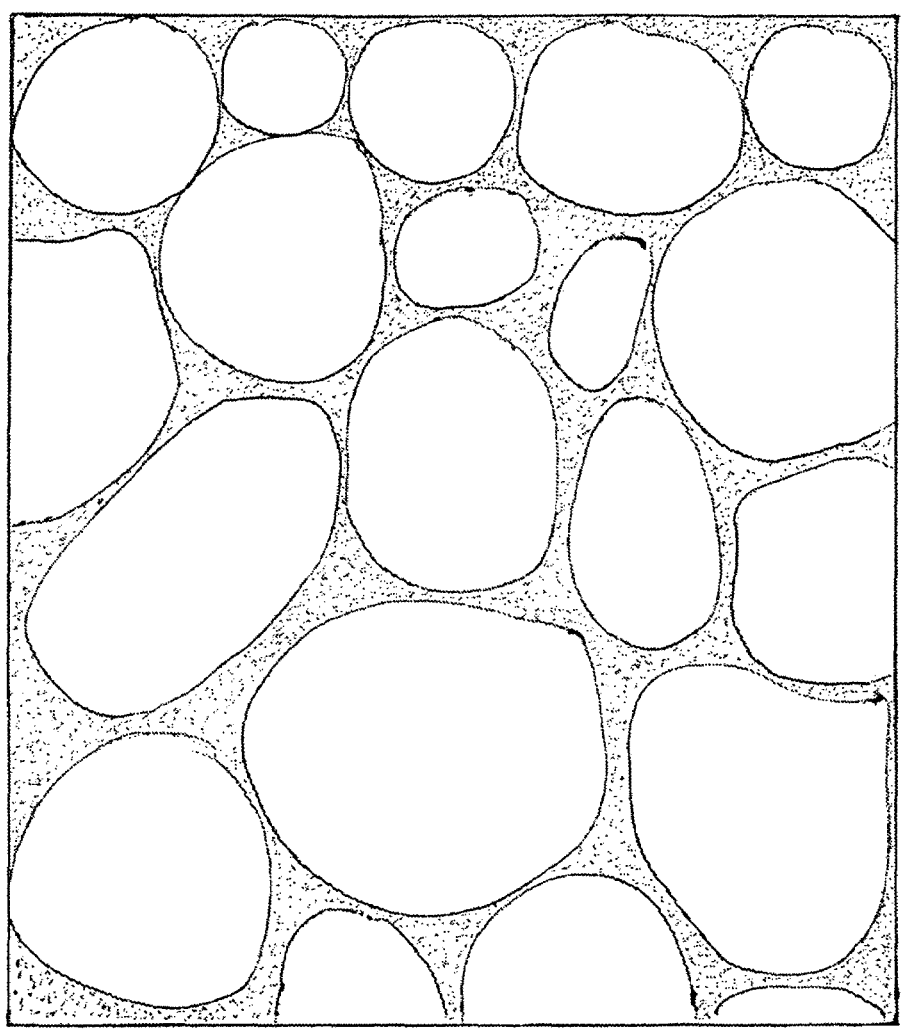
FIG. 1. Schematic representation: The open (white) circles represent the original particles of the powder compounds (solid part) which are bound together by the components applied in liquid form (liquid part), shown as dotted areas between the circles.

In contrast to the standard lyophilisation processes used in the preparation of fast-disintegrating solid dosage forms, which are laborious, expensive and energy intensive, the present invention uses a highly economical process and novel rationalized lyophilisation technology for the manufacture of solid highly porous fast-disintegrating dosage forms.

In the method of the invention, structure building components are applied in solid powder form. Structure building components, optionally comprising tablet fillers and other excipients, are compounds which provide the required shape and tensile strength of the product, as will be described in more detail hereinbelow. The active ingredient may also be provided wholly or partially in solid powder form. The remaining compounds to be dissolved in water comprise binders, as will be described hereinbelow, and optionally other excipients, in particularly those who should be present in molecularly dispersed form. For example, the active ingredient may be dissolved in water.

The freezing step is done in a conventional manner. Temperatures are below −20° C., for example between −20° C. and −50° C., e.g. around −30° C. Water is sublimated reduced pressure, e.g. below 6.11 mbar (6.11×10⁻⁸ Pa), for example in high vacuum, e.g. at about 1 mbar to 0.01 mbar (1×10⁻⁸ to 1×10⁻¹⁰ Pa).

Optional further steps in the method of the invention comprise sealing of the blister packs or transferring the resulting products from the moulds into suitable packaging.

A particular application is in the field of pharmaceuticals where the process will be applied for oral fast-disintegrating dosage forms. In this process only the active ingredient or particular components which should be incorporated in molecularly dispersed form will be lyophilised. The novel oral dosage forms obtained are highly porous shaped objects as pharmaceutical tablet-like discs or sheets or tablet of another shape, which rapidly incorporate water when taken into the mouth, decompose immediately und therefore are easily digested.

The same procedure may also be applied for other dosage forms for use in veterinary medicine, food products or technical applications. Fast-disintegrating dosage forms are important in a number of different fields of application. For example they may be used for textile washing or in dishwashers, and comprise detergents and suitable additives. Other applications are e.g. as bleaching tablets, sanitization tablets, water treatment tablets, denture cleansing tablets, and for decalcification of apparatus running with hot water, e.g. coffee machines, hot water pots, and nozzles in showers, and the like.

Another particular application of fast-disintegrating dosage forms is in the field of foodstuffs, e.g. for coffee, tea, cocoa or powdered milk, gravy, soup or other drinks, where the tablet is to be dissolved in cold or hot water to reconstitute the original foodstuff, or in tablets of edible energy source to be taken directly into the mouth without water, e.g. fast energy providers to be eaten and digested during periods of continuous activity such as running or biking and similar sports.

The new process of manufacture uses a targeted, reduced, partial lyophilisation process which requires a reduced amount of water and remains without biopharmaceutical or technological drawbacks compared to standard lyophilisation. For example, whereas in a standard lyophilisation process the solution or suspension to be freeze-dried usually contains around 10% (w/w) of solids and 90% water, or in extreme cases up to 20% solids and 80% water, the present procedures actually uses less than 80% (w/w) water, e.g. between 20% and 70%, preferably between 30% and 40% water. As a consequence this process saves a substantial amount of energy and time. In a standard lyophilization process, e.g. the one described in U.S. Pat. No. 4,371,516, all the components are provided as a solution or dispersion in water, and then the water is sublimed. The present invention, however, uses much less water, since the structure building components and optionally the active ingredient are applied in solid powder form, i.e. neither as a solution nor a dispersion in water.

For pharmaceutical applications, the resulting products are preferably in the form of small disks, rods or sheets, but can also be termed tablets, although these products do not represents tablets in the usual sense obtainable by compression. On oral application through the buccal cavity, for example when putting on the moist tongue, they rapidly take up water from saliva, mollify, disintegrate immediately, or are easily chewed or crushed with the tongue. For patients having problems ingesting standard oral dosage forms, in particular small children and elderly patients, it is a welcome simplification when the pharmaceutical compound is dissolved immediately on ingestion without additional liquid. If it is not completely dissolved there will be a pasty mass easily swallowable. In this respect the products of the present invention do not principally differ from pharmaceutical oral dosage forms prepared according to the well known Zydis® technology or related processes.

The novel process of manufacture largely depends on the known classical lyophilisation processes. As a characteristic aspect of the new technology the total amount of the mass to be formed into the required dosage form is partitioned into two parts, one liquid part and one solid part, which are dosed separately. In more detail the procedure consists of the following steps: First the components of the formulation are selected which do not have to be dissolved and lyophilized for biopharmaceutical or technological reasons, but can be introduced in a solid, powder-like form. These components are intimately mixed. For pharmaceutical oral dosage forms components suitable for solid handling are in particular structural components, e.g. sugar alcohols such as mannitol or xylitol, sugars, such as saccharose, glucose, lactose, fructose, and the like. It may also be advisable to incorporate other components used as fillers or excipients, for example preservatives, stabilizers, wetting agents and/or emulsifiers, solubilizers, salts for regulating osmotic pressure and/or buffers, for example glycine, starches, dicalcium phosphate, microcrystalline cellulose, aroma compounds, dyestuffs and pigments, solid buffers and similar compounds. Fillers are able to build up porous structures, support rapid disintegration and preferably have a non-hygroscopic character. This solid powder mixture may also contain the active ingredient if this is not completely soluble in the aqueous phase, or if it is not advisable for biopharmaceutical reasons to incorporate it in dissolved form, for example if a prolonged activity of the active ingredient is desired.

The liquid part consists of an aqueous solution comprising the active ingredient and binding agents as the main components. Suitable binding agents selected for the purpose are selected from the usual tablet binding agents which show good binding properties and also support the structural stability of the lyophilisate, for example hydrolysed or non-hydrolysed gelatine, polyvinylpyrrolidone (Kollidon®), cellulose ether, pre-gelatinised starch and the like. Also small amounts of other excipients, for example preservatives, stabilizers, wetting agents and/or emulsifiers, solubilizers, salts for regulating osmotic pressure and/or buffers may be dissolved, if it makes sense from a biopharmaceutical or technological aspect, in particular surface active, wetting agents. The optimised, reduced amount of water required is determined for each case in preliminary tests. For that purpose an experiment using the solid part of the formulation will be taken and increasing amounts of the liquid part added to it to determine the minimum amount of liquid resulting in a homogenous plasticized and thoroughly moistened, mouldable mass.

For non-pharmaceutical applications the choice of structural components, binders and other excipients is, of course, adapted to the envisaged use, but follows the same principles, i.e. limiting the amount of components to be provided in dissolved form such as to minimize the total amount of water.

In the method of the invention the solid part comprises at least 30% of the total weight of the solid dosage form components (including water to be sublimed in the process), preferably more than 50%, most preferably more than 75%. The lower the amount of water required, the higher the savings in sublimation time and energy in the last step of the process.

DETAILED DESCPRIPTION OF THE DRAWINGS

The highly porous, fast-disintegrating solid dosage form obtained in the process of the invention is schematically illustrated in FIG. 1. The open (white) circles represent the original particles of the powder compounds (solid part) which are bound together by the components applied in liquid form (liquid part), shown as dotted areas between the circles. On adding the liquid part with the dissolved components to the solid dosed powder, the liquid enters into the remaining open spaces of the solids, and is distributed evenly. On cooling and evaporating, freeze-drying only takes place in these (dotted) spaces, whereas the solid, not dissolved parts (white) are not directly involved, but are pasted together in the lyophilisation process. A matrix is formed wherein the solid powder components may be regarded as "bricks" pasted together with "mortar" to give a solid "brick structure", corresponding to a film-coated, aerogel-like network structure, wherein the solid "bricks" have a diameter of between 0.025 mm and 2 mm, in particular 0.1 and 1.5 mm. On application of this solid dosage form, e.g. as a pharmaceutical oral dosage form taken on the moist tongue, water (saliva) enters into the hollow spaces of the freeze-dried network structure and dissolves the components of the original liquid part almost instantaneously. As a consequence the components of the original solid powder part of the matrix are set free, and the "brick structure" collapses. The powder particles will then be dissolved with a dissolution velocity corresponding to their standard solubility.

Figure 2:
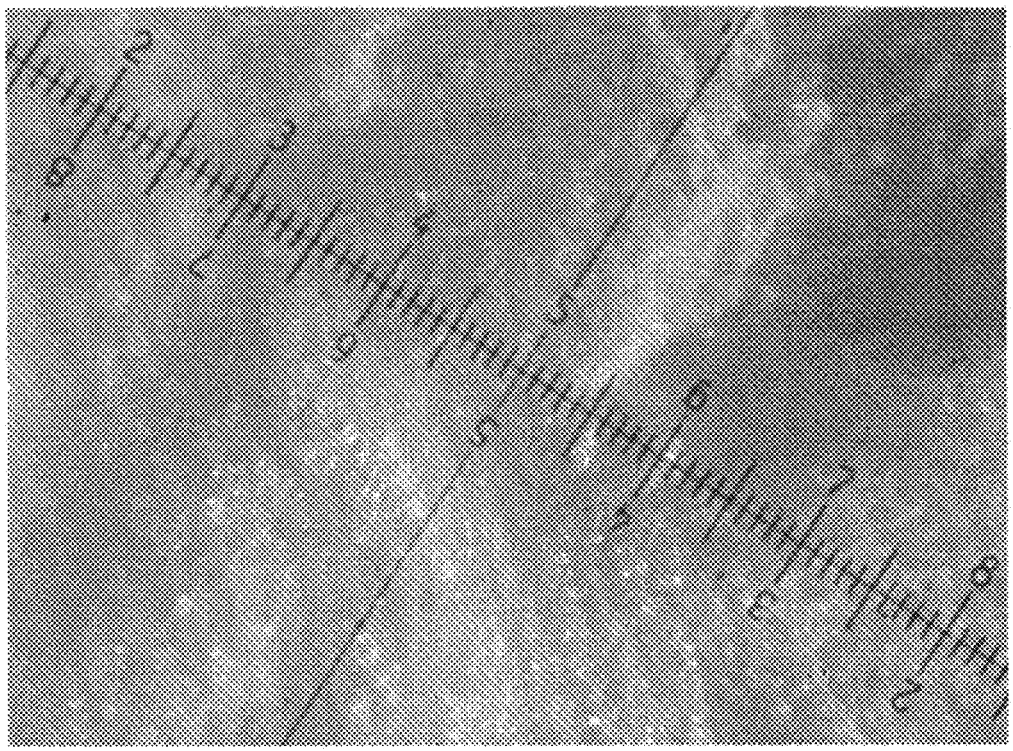
FIG. 2. Microscopic pictures of lyophilized loperamid, one unit representing 0.01562 mm, every tenth being numbered; in the upper picture loperamid produced with the Zydis® technology described in EP 295 242; in the lower picture loperamid produced with the method of the invention, Example 1.
Figure 2:
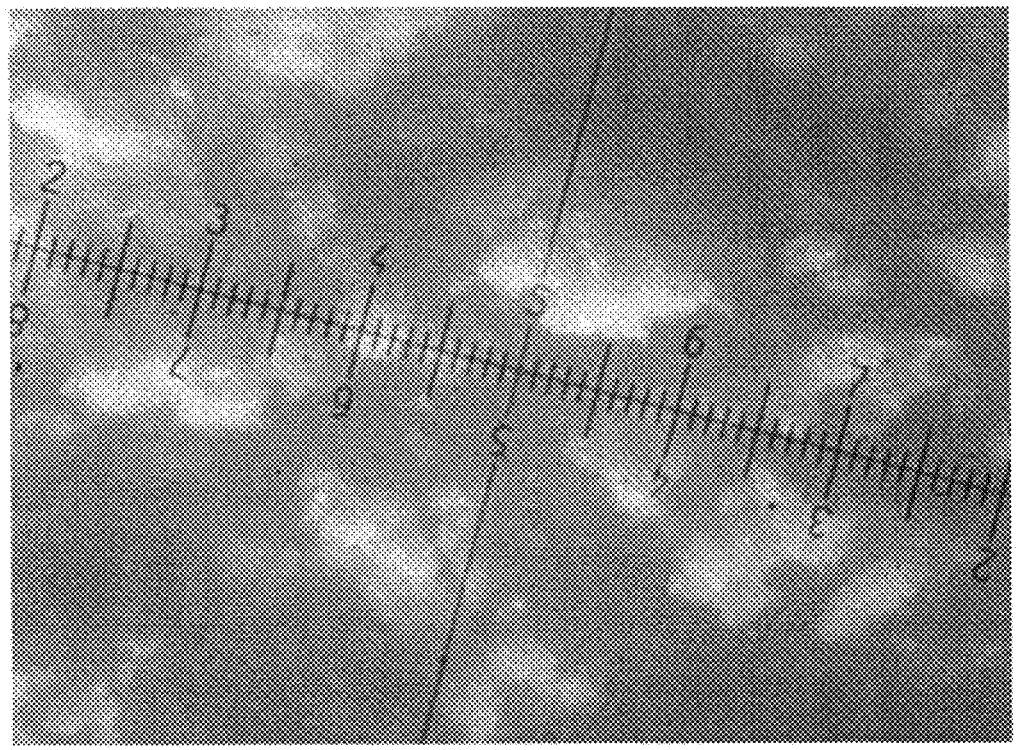

FIG. 2 shows microscopic pictures of lyophilised loperamid, one unit representing 0.01562 mm, every tenth being numbered (i.e. ten units representing 0.1562 mm); in the upper picture loperamid produced with the Zydis® technology described in EP 295 242 giving rise to evenly dispersed solids; in the lower picture loperamid produced with the method of the invention, Example 1, demonstrating lumps ("bricks") of solid material corresponding to the schematic representation of FIG. 1.

In a suitable apparatus for filling, dosing, and packing, for example packing into blister packs, the lower foil is prepared to contain cavities, and in these cavities (the lower part of a blister pack) an exactly measured amount of each of the solid part and of the liquid part is added and combined. This may be performed directly in the cavities of the blister foils or in other suitable moulding equipment. The single doses of plasticized and moistened mass so formed are then introduced into a standard lyophilisation apparatus, for example an apparatus used for standard Zydis® technology, and frozen to −20° to −50° C. The frozen intermediates are further transported into the high vacuum part of the apparatus where the residual water is removed completely or almost completely by sublimation.

This new process of reduced partial lyophilisation only requires lyophilisation of that part of the total mass for which there is a biopharmaceutical or technological reason to introduce it in liquid form. The other components of the formulation, as a rule representing the main part, will only be introduced in solid powder form. This is a more rationalized process for the manufacture of suitable sturdy, highly porous dosage forms, which disintegrate already in the presence of small amounts of water, and therefore can be easily ingested and swallowed if designed for immediate consumption, or rapidly dissolved in water. The procedure may also be termed containment process since it allows the manufacture of a dosage form in one step using one apparatus from start to end providing the final package ready for distribution.

Active ingredients are especially pharmaceuticals but may also be, for example, vitamins, minerals or dietary supplements. Pharmaceuticals may include, without limitation, antacids, analgesics, anti-inflammatory agents, antibiotics, laxatives, anorexics, anti-asthmatics, diuretics, antiflatulents, antimigraine agents, anti-arrhythmic agents, antispasmodics, sedatives, antihyperactive agents, tranquilizers, antihistamines, decongestants, beta-blockers, coronary vasodilators, bronchodilators, muscle relaxants, anticoagulants, antileptic agents, anti-emetics, hypotensives, sympathomimetic agents, expectorants, oral antidiabetic agents, hormones and combinations thereof.

The active pharmaceutical ingredients for this new process may be dissolved, partially dissolved or mixed in the solid state, in pure form or in a special pre-treated form. The active ingredients may be present as optical isomers, different crystal modifications, in particular corn size or particular shape. Pre-treated active ingredients are, for example, coated active ingredients, such as micro- or nano-encapsulated, or imbedded to fulfil particular functions, e.g. with enteric coating for acid-labile compounds, or as retard forms to control bioavailability over an extended period of time.

Excipients used with the new technology are those which are also known from traditional preparation of oral dosage forms, for example for compressed tablets, such as fillers and structural components, e.g. sugar alcohols, sugars, cellulose powder, dicalcium phosphate, calcium sulphate, microcrystalline cellulose and the like, also binders with suitable binding ability and properties supporting formation of a sturdy structure of the lyophilisate, e.g. gelatine, povidone, soluble cellulose ether and the like. The binding agent is primarily used to give sufficient consistency to the formulation to avoid breaking of the article when removed from blisters and during handling. Further excipients considered are also the usual disintegrators, e.g. starches and super disintegrators, hydrophilizers, solubilizers, aroma compounds and sweeteners.

The expression "tablets" as used herein is not limited to a particular size or form of the oral dosage form. Tablets may have many different appearances, such as classical dish-like shapes, but also other spherical or ellipsoid shapes, rods, granules, blocks, cubes with rounded edges, or particular forms as obtainable from a suitable mould. Size may vary from approximately 1.5 mm diameter or 1.5 mm extension in the longest direction, so-called micro-tablets or pellets, to approximately 20 mm, preferably in the range of 2 to 10 mm. For non-pharmaceutical uses, e.g. as "tablets" comprising foodstuff to be dissolved in water, for veterinary uses or as "tablets" containing chemicals for use in technical processes, the size may be considerably larger, e.g. up to the size of a golf ball.

As is readily understandable from the description of the method of the invention, this procedure is less time-consuming and less energy-consuming than the standard lyophilisation process wherein the amount of water to be removed by freeze-drying is considerably greater. On the other hand, tablet-like oral dosage forms are obtained with a similar porous structure as usually result from standard freeze-drying processes.

Oral pharmaceutical dosage forms so produced may immediately be packed into suitable containers for transport and use, for example regular or peel-of blister packs, depending on the property of the tablet components and their tensile strength.

As a result of the particular process of manufacture used, the dosage form of the invention normally has a density of 200-1000 mg/ml, preferably 300-900 mg/ml, more preferably 600-900 mg/ml, or 400-800 mg/ml. This is a density that is much lower than that of compressed dosage forms like normal tablets (having densities of above 1000 mg/ml). As a result of its unusually low density, the dosage form of the invention disintegrates more rapidly than would be the case, if the mixture of its components are subjected to compression force.

The following examples illustrate the invention, but in now way limit the scope thereof.

EXAMPLE 1

Loperamid Fast-Disintegrating Tablets, Standard Active Ingredient

Sodium hydrogen carbonate (1.0 kg) and peppermint essence powder (0.01 kg) are mixed to homogeneity portion by portion with mannitol (244.38 kg) in a mixer with stirring to give part I as a powder. Gelatine (0.6 kg) is dissolved in water (50 kg) by slight heating. Aspartam (0.01 kg) is added to the solution, followed by loperamide hydrochloride (4.0 kg) to give part II as a solution.

In a blister pack apparatus suitable for lyophilisation exactly measured portions of powder (part I) are dosed into cavities of the blister pack lower foil. In a second step exactly measured portions of the solution (part II) are added. The blister foil with the filled cavities is transported into the freeze part of the blister pack apparatus and frozen at the temperature between −20° and −50° C. After freezing the water is evaporated (sublimed) in high vacuum. The weight of the single portions of dried tablets of sufficient tensile strength is 125 mg. At the end the blister packs are sealed with a cover foil and further packed into suitable packing using standard procedures.

EXAMPLE 2

Ibuprofen Fast-Disintegrating Tablets, Sparingly Soluble Active Ingredient

Ibuprofen (20.0 kg) and orange essence powder (0.3 kg) are mixed to homogeneity portion by portion with mannitol (171.6 kg) in a mixer with stirring to give part I as a powder. Hydrolized gelatine (3.0 kg), aspartam (0.1 kg) and mannitol (5.0 kg) are dissolved in water (50 kg) by slight heating to give part II as a solution.

In a blister pack apparatus suitable for lyophilisation exactly measured portions of powder (part I) are dosed into cavities of the blister pack lower foil. In a second step exactly measured portions of the solution (part II) are added. A moist plasticized mass is obtained containing the precise amounts of the components of each tablet. The blister foil with the filled cavities is further treated as described in Example 1 to give single portions of dried tablets of sufficient tensile strength weighing 200 mg.

EXAMPLE 3

Acetylsalicylic Acid Fast-disintegrating Tablets, Stabilized and Coated Active Ingredient Acetylsalicylic acid (300.0 kg) is stabilized by mixing with an ethanolic solution of anhydrous citric acid (30.0 kg) in ethanol, and evaporated to dryness. The stabilized acetylsalicylic acid crystals are then coated with aqueous ethanolic ethylcellulose (8%, 125.0 kg) according to standard procedures in a fluidized bed reactor, and dried, resulting in approx. 340 kg of product. This product is intimately mixed with mannitol (537.0 kg), saccharin sodium (sweetener, 1.0 kg) and raspberry flavour powder in a mixer with stirring to give part I as a powder. Polyvinylpyrrolidone (8.0 kg) and mannitol (10.0 kg) are dissolved in deionized water (180 kg) by slight heating to give part II as a solution. In a blister pack apparatus suitable for lyophilisation exactly measured portions of powder (part I) are dosed into cavities of the blister pack lower foil. In a second step exactly measured portions of the solution (part II) are added. A moist plasticized mass is obtained containing the precise amounts of the components of each tablet. The blister foil with the filled cavities is further treated as described in Example 1 to give single portions of dried tablets of sufficient tensile strength weighing 300 mg.

EXAMPLE 4

5-Aminosalicylic Acid Fast-Disintegrating Tablets, Pre-Formed Pellets with Active Ingredient Saccharose powder (75 kg), corn starch (8 kg) and sodium carboxymethyl starch (Vivistar P®, 2.5 kg) are intimately mixed to homogeneity. Pre-coated pellets of 5-amino-salicylic acid (100 kg) are evenly distributed in the mixed powder to give the solid part I. Gelatine (3 kg), mannitol (11 kg) and caramel flavour (0.5 kg) are dissolved in water (approx. 60 kg) with slight heating to give part II as a solution.

In a blister pack apparatus suitable for lyophilisation exactly measured portions of powder (part I, 1.855 g) are dosed into cavities of the blister pack lower foil. In a second step exactly measured portions of the solution cooled to room temperature (part II, 0.745 g) are added. The blister foil with the filled cavities containing the thoroughly wetted mass is frozen at −30° C. In the next step the water is sublimed in high vacuum, and the blister packs sealed by a cover foil. The single portions of dried tablets are of sufficient tensile strength and contain 2.0 g of product.

EXAMPLE 5

Decalcification Agent

Sodium hexametaphosphate (980 g), tetrasodium pyrophosphate (6.0 g), polyacrylic acid (0.5 g) and sodium metaphosphate (3.5 g) are mixed to homogeneity in a mixer with stirring to give part I as a powder. Sodium carbonate (10.0 g) is dissolved in water (100 g) to give the liquid part II. The solid powder (part I) is first measured into the cavities of a blister pack lower foil. Then each dose of the powder part I is moistened thoroughly with a measured dose of the liquid part II. The blister foil with the filled cavities is further treated as described in Example 1 to give single portions of dried tablets of sufficient tensile strength weighing 1 g, suitable for rapid dissolution in water for decalcification.

EXAMPLE 6

Peppermint Essence

Standardized peppermint extract (1.5 kg) and mannitol (1.5 kg) are mixed with a stirrer to homogeneity to give part I as a powder. Saccharose (0.3 kg) is dissolved as a binder in water (0.6 kg) to give the liquid part II. The solid powder (part I) is dosed in measured amounts into cavities of a blister pack lower foil, and homogeneously moistened with the measured dose of part II. The blister foil with the filled cavities is further treated as described in Example 1 to give single portions of dried tablets of sufficient tensile strength weighing 3 g, suitable for rapid dissolution in hot water for preparation of peppermint tea.

EXAMPLE 7

Furosemid

Citric Acid (30.0 kg) are homogeneously mixed with mannitol (100.0 kg) and colloidal silica (0.5 kg) to give part I as a powder. Furosemide-sodium (50.0 kg) are suspended and dissolved, as far as possible, together with povidone 30 (1.5 kg), aspartame (0.05) and mannitol (17.95 kg) in water (about 70.0-80.0 kg) to give the liquid part II. In a blister pack apparatus suitable for lyophilisation exactly measured portions of powder (part I) are dosed into cavities of the blister pack lower foil. In a second step exactly measured portions of the solution (part II) are added. The blister foil with the filled cavities is transported into the freeze part of the blister pack apparatus and frozen at the temperature between −200 and −50° C. After freezing the water is evaporated (sublimed) in high vacuum. The weight of the single portions of dried tablets of sufficient tensile strength is 100 mg. A single dose of the drug Furosemide-sodium is 25 mg per tablet. At the end the blister packs are sealed with a cover foil and further packed into suitable packing using standard procedures.

EXAMPLE 8

Flurbiprfen

Sodium Carbonate (30.0 kg) are homogeneously mixed with mannitol (50.0 kg) and colloidal silica (0.3 kg) to give part I as a powder. Flurbiprofen-acid (10.0 kg) are suspended in the solution of hydrolysed gelatin (1.5 kg), saccharin-sodium (0.05) and mannitol (28.15 kg) in water (about 40.0 kg) to give the liquid part II. In a blister pack apparatus suitable for lyophilisation exactly measured portions of powder (part I) are dosed into cavities of the blister pack lower foil. In a second step exactly measured portions of the solution (part II) are added. The blister foil with the filled cavities is transported into the freeze part of the blister pack apparatus and frozen at the temperature between −20° and −50° C. After freezing the water is evaporated (sublimed) in high vacuum. The weight of the single portions of dried tablets of sufficient tensile strength is 70 mg. A single dose of the drug Flurbiprofen-acid is 5 mg per tablet. At the end the blister packs are sealed with a cover foil and further packed into suitable packing using standard procedures.

The invention claimed is:

1. A method of manufacture of a fast-disintegrating solid dosage form comprising steps (a)-(d), wherein:
   step (a) comprises dosing a mixed solid powder comprising one or more structure building components into cavities of blister packs or moulds,
   step (b) consists of dissolving a binder, and optionally a remaining component selected from the group consisting of an excipient, a solubilizer, a salt, a buffer, a wetting agent and an active ingredient, in water to form an aqueous solution, and then dosing the aqueous solution into the cavities with the powder to form a moistened, plasticized mass, wherein the amount of water in the aqueous solution is from 20% to 70% (w/w) of the total weight of all of the components of the fast-disintegrating solid dosage form,
   step (c) comprises freezing to below −20° C., and
   step (d) comprises subliming frozen water under high vacuum.

2. The method of claim 1 for the manufacture of a solid dosage form comprising a pharmaceutically active ingredient, wherein the solid dosage form is an oral dosage form.

3. The method of claim 1 for the manufacture of a solid dosage form comprising a foodstuff.

4. The method of claim 2 wherein the structure building components comprise sugar alcohols or sugars.

5. The method of claim 4 wherein the structure building components further comprise fillers or other excipients.

6. The method of claim 1 wherein the binder is selected from the group consisting of hydrolysed or non-hydrolysed gelatine, polyvinylpyrrolidone, cellulose ether, and pre-gelatinised starch.

7. The method of claim 2 wherein the active ingredient is selected from the group consisting of antacids, analgesics, anti-inflammatory agents, antibiotics, laxatives, anorexics, anti-asthmatics, diuretics, antiflatulents, antimigraine agents, anti-arrhythmic agents, antispasmodics, sedatives, antihyperactive agents, tranquilizers, antihistamines, decongestants, beta-blockers, coronary vasodilators, bronchodilators, muscle relaxants, anticoagulants, antileptic agents, antiemetics, hypotensives, sympathomimetic agents, expectorants, oral antidiabetic agents, hormones and combinations thereof.

8. The method of claim 7 wherein the active ingredient is selected from the group consisting of loperamid, ibuprofen, acetylsalicylic acid, 5-aminosalicylic acid, furosemid, and flurbiprofen.

9. The method of claim 7 wherein the active ingredient is micro- or nano-encapsulated, enteric coated or in a retard form.

10. The method of claim 1 wherein the solid powder comprises at least 30% (w/w) of the total weight of the solid dosage form components including water to be sublimed in the process.

11. The method of claim 10 wherein the solid powder comprises at least 50% (w/w) of the total weight of the solid dosage form components including water to be sublimed in the process.

12. The method of claim 10 wherein the solid powder comprises at least 75% (w/w) of the total weight of the solid dosage form components including water to be sublimed in the process.

13. The method of claim 1 wherein the amount of water in the aqueous solution is from 30% to 40% (w/w) of the total weight of all of the components of the fast-disintegrating solid dosage form.

* * * * *